United States Patent
Selby et al.

(10) Patent No.: US 6,660,471 B2
(45) Date of Patent: Dec. 9, 2003

(54) ENHANCED REPLICATION OF HCV RNA

(75) Inventors: Mark Selby, San Francisco, CA (US); Hui-Hua Lu, Foster City, CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/922,962

(22) Filed: Aug. 3, 2001

(65) Prior Publication Data

US 2002/0142455 A1 Oct. 3, 2002

Related U.S. Application Data

(60) Provisional application No. 60/223,244, filed on Aug. 4, 2000.

(51) Int. Cl.[7] .............................. C12Q 1/00; C12Q 1/70; G01N 33/576; C12N 5/08; C12N 7/06
(52) U.S. Cl. .............................. 435/5; 435/4; 435/7.21; 435/325; 435/235.1; 435/238; 435/366; 435/370
(58) Field of Search ................................ 435/4, 5, 7.21, 435/325, 235.1, 238, 366, 370

(56) References Cited

U.S. PATENT DOCUMENTS 5,840,565 A * 11/1998 Lau .................. 435/235.1

OTHER PUBLICATIONS

Bartenschlager et al. Journal of General Virology 2000, vol. 81, pp. 1631–1648.*

Behrens et al., "Characterization of an Autonomous Subgenomic Pestivirus RNA Replicaon," *Journal of Virology* 72(3):2364–2372 (1998).

Dubensky et al., "Sindbis Virus DNA–Based Expression Vectors: Utility for In Vitro and In Vivo Gene Transfer," *Journal of Virology* 70(3):508–519 (1996).

Lohmann et al., "Replication of Subgenomic Hepatitis C Virus RNAs in a Hepatoma Cell Line," *Science* 285:110–113 (1999).

Vassilev et al., "Authentic and Chimeric Full–Length Genomic cDNA Clones of Bovine Viral Diarrhea Virus That Yield Infectious Transcripts," *Journal of Virology* 71(1):471–478 (1997).

* cited by examiner

*Primary Examiner*—James Housel
*Assistant Examiner*—Bao Qun Li
(74) *Attorney, Agent, or Firm*—Roberta L. Robins; Alisa A. Harbin; Robert P. Blackburn

(57) ABSTRACT

This invention provides methods of generating cells that stably replicate sub-genomic virus replicons. This invention also provides methods of generating cells that have disabled PKR activity and that stably replicate HCV sub-genomic replicons. The invention also provides methods of using the cells of the invention to screen for compounds that modulate viral RNA replication, including HCV RNA replication.

6 Claims, No Drawings

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:
    PKR-specific oligonucleotide primer 1

<400> SEQUENCE: 1
agcttccaac caggatacgg                    20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence:
    PKR-specific oligonucleotide primer 2

<400> SEQUENCE: 2
ggctctaaca tgtgtgtcgt tc                 22

<210> SEQ ID NO 3
<211> LENGTH: 50
<212> TYPE: DNA
<213> ORGANISM: Artificial Sequence
<220> FEATURE:
<223> OTHER INFORMATION: Description of Artificial Sequence:
    mutagenesis primer 1

<400> SEQUENCE: 3
cggaaagact tacgttatta gacgtgttaa atataataac gagaaggcgg    50

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence:
    mutagenesis primer 2

<400> SEQUENCE: 4
ccgccttctc gttattatat ttaacacgtc taataacgta agtctttccg    50

ENHANCED REPLICATION OF HCV RNA

CROSS-REFERENCE TO RELATED APPLICATION

This application is related to provisional patent application serial No. 60/223,244, filed Aug. 4, 2000 from which priority is claimed under 35 USC §119(e)(1) and which is incorporated herein by reference in its entirety.

FIELD OF THE INVENTION

The present invention relates to the generation of cellular environments that are favorable for the replication of sub-genomic hepatitis C virus (HCV) replicons. The present invention also relates to use of cells presenting such replicon replication-favorable environments to screen for compounds useful for the treatment of HCV infection and related diseases.

BACKGROUND OF THE INVENTION

Because of the large number of HCV infected individuals worldwide, therapeutic drugs are critically needed. Currently, it is not possible to efficiently propagate HCV in culture, or to generate actively infected non-primate animal models of the disease.

The efforts to develop therapeutic drugs against HCV would be aided by the establishment of cell lines that carry replicating HCV RNA or synthesize de novo HCV virus. In particular, a reproducible system which accommodates replication of sub-genomic RNA would facilitate drug screening. However, no such system currently exists that is both robust and amenable to drug screening applications. Recently, Lohmann et al. (1999, Science, 285:110–113) described neomycin-selectable, HCV sub-genomic replicons, which were used to establish a few stable cell clones producing autonomously replicating sub-genomic HCV RNAs, in Huh-7 cells. Lohmann et al. report that efficiency of recovery, however, was low, and speculate that recovery was due to particular host cell conditions or factors present in only a few cells.

The present invention is directed to a cell-based system to establish the replication of sub-genomic viral replicons, such as that of HCV, with high efficiency.

SUMMARY OF THE INVENTION

The present invention is directed to methods of generating cells, with a disabled host anti-viral response factor, that stably replicate sub-genomic virus replicons. In one aspect, the methods comprise disabling PKR activity in a cell prior to or concurrent with introducing a sub-genomic virus replicon into the cell. Preferably, the sub-genomic virus replicon is an HCV sub-genomic replicon.

In a further aspect, the present invention is directed to cells that are generated according to the aforementioned methods. These cells have disabled PKR activity and stably replicate sub-genomic virus RNA.

In yet another aspect, the present invention is directed to methods of screening for compounds that modulate viral RNA replication.

These and other aspects of the invention are described more fully below.

All publications, patents and patent applications cited herein are hereby incorporated by reference in their entirety.

DETAILED DESCRIPTION OF THE INVENTION

HCV is an enveloped, positive-strand (messenger sense) RNA virus belonging to the family Flaviviridae. The HCV genome is a single-stranded RNA of about 9.5 kb in length. Like other single-stranded RNA viruses, HCV is believed to replicate its genomic RNA via a double-stranded RNA (ds-RNA) intermediate.

The HCV genome codes for a polyprotein that is subsequently spliced and processed into the structural proteins C (core) and E1, and E2 (both envelope proteins) and the non-structural proteins (NS2, NS3, NS4A, NS4B, NS5A, NS5B) of the virus. The positions of the various proteins produced from the polyprotein, numbered relative to HCV-1 (see, Choo et al. (1991) *Proc. Natl. Acad. Sci. USA* 88:2451–2455) is shown in Table 1.

TABLE 1

| Domain | Approximate Boundaries* |
| --- | --- |
| C (core) | 1–191 |
| E1 | 192–383 |
| E2 | 384–746 |
| P7 | 747–809 |
| NS2 | 810–1026 |
| NS3 | 1027–1657 |
| NS4a | 1658–1711 |
| NS4b | 1712–1972 |
| NS5a | 1973–2420 |
| NS5b | 2421–3011 |

*Numbered relative to HCV-1. See, Choo et al. (1991) Proc. Natl. Acad. Sci. USA 88:2451–2455.

It is well documented that virus infection triggers an interferon response in the host, including the induction of the expression of the cellular ds-RNA-dependent protein kinase (PKR). PKR becomes activated, through autophosphorylation, upon binding to viral ds-RNA. Activated PKR phosphorylates the eukaryotic translation initiation factor 2 (eIF2α), leading to a dramatic reduction in both cellular and viral protein synthesis. This, among other interferon-induced effects, results in apoptosis of infected cells.

The difficulty in obtaining HCV replicon-transfected cell clones may be related to the induction of the activation of PKR by the viral ds-RNA in the cells. Therefore, blocking PKR activity would be expected to facilitate the establishment of clones of cells that are capable of stably replicating HCV viral replicons.

Cells deficient in PKR activity have been described for the generation of viral vaccines and persistent viral infections (U.S. Pat. No. 5,840,565; Yeung et al., 1999, Proc. Natl. Acad. Sci. USA, 96:11860–11865). In these systems, persistent infections are established when cell cultures are infected with virus particles, i.e., complete viral genomes, for the generation of progeny virus. These systems have not been applied to the generation of stable cell lines capable of replicating sub-genomic viral replicons, nor have they been applied to HCV.

The invention provides, inter alia, methods to prepare cells, having disabled PKR activity, for the replication of sub-genomic viral replicons, preferably HCV sub-genomic replicons. The invention also provides methods of using these cells to screen for drugs that modulate viral replication.

The practice of the present invention will employ, unless otherwise indicated, conventional methods of virology, immunology, microbiology, molecular biology and recombinant DNA techniques within the skill of the art. Such techniques are explained fully in the literature. See, e.g., Maniatis et al., eds., Molecular Cloning: A Laboratory Manual ($2^{nd}$ ed.) Cold Spring Harbor Laboratory Press, Cold Spring Harbor, N.Y. (1989); Glover, ed., DNA Cloning: A Practical Approach, Vols. I & II; Colowick & Kaplan, eds., Methods in Enzymology, Academic Press; Weir & Blackwell, eds., Handbook of Experimental Immunology, Vols. I–IV Blackwell Scientific Pubs. (1986); Fields, Knipe, & Howley, eds., Fields Virology, 3$^{rd}$ Edition, Vols. I &II, Lippincott Williams & Wilkins Publishers (1996); Coligan et al., eds., Current Protocols in Immunology, John Wiley & Sons, New York, N.Y. (2000).

Various definitions are made throughout this document. Most words have the meaning that would be attributed to those words by one skilled in the art. Words specifically defined either below or elsewhere in this document have the meaning provided in the context of the present invention as a whole and as typically understood by those skilled in the art.

As used herein, the term "replicon" refers to a viral nucleic acid that is capable of directing the generation of copies of itself. As used herein, the term "replicon" includes RNA as well as DNA. For example, double-stranded DNA versions of HCV genomes can be used to generate a single-stranded RNA transcript that constitutes an HCV replicon. Generally, a viral replicon contains the complete genome of the virus. "Sub-genomic replicon," as used herein, refers to a viral nucleic acid that contains something less than the full complement of genes and other features of the viral genome, yet is still capable of directing the generation of copies of itself. For example, the sub-genomic replicons of HCV described below contain most of the genes for the non-structural proteins of the virus, but are missing most of the genes coding for the structural proteins. Sub-genomic replicons are capable of directing the expression of all of the viral genes necessary for the replication of the viral sub-genome (replication of the sub-genomic replicon), without the production of viral particles.

An HCV sub-genomic replicon, may be derived from any of the various HCV strains and isolates, such as, but not limited to, any of the isolates from strains 1, 2, 3, 4, 5 or 6 of HCV. Moreover, the various genes included in the sub-genomic replicon can be derived from different strains. The complete genotypes of many of these strains are known. See, e.g., U.S. Pat. No. 6,150,087 and GenBank Accession Nos. AJ238800 and AJ238799, International Publication Nos. WO 89/04669; WO 90/11089; and WO 90/14436. Moreover, the genes included in the sub-genomic replicon may be full-length, fragments or variants of the native sequence, so long as the sub-genomic replicon remains capable of expressing the viral genes necessary for replication thereof, without producing viral particles. Thus, for example, the genes included in the sub-genomic replicon may be homologous to the native genes. "Homology" refers to the percent similarity between two polynucleotide or two polypeptide moieties. Preferably, the sequences will exhibit at least about 50%, preferably at least about 75%, more preferably at least about 80%–85%, preferably at least about 90%, and most preferably at least about 95%–98% sequence similarity or identity over a defined length of the molecules, or any integer between these values. In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100.

Readily available computer programs can be used to aid in the analysis of homology and identity, such as ALIGN, Dayhoff, M. O. in *Atlas of Protein Sequence and Structure* M. O. Dayhoff ed., 5 Suppl. 3:353–358, National biomedical Research Foundation, Washington, DC, which adapts the local homology algorithm of Smith and Waterman *Advances in Appl. Math.* 2:482–489, 1981 for peptide analysis. Programs for determining nucleotide sequence homology are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent homology of a particular nucleotide sequence to a reference sequence can be determined using the homology algorithm of Smith and Waterman with a default scoring table and a gap penalty of six nucleotide positions.

Another method of establishing percent homology in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence homology." Other suitable programs for calculating the percent identity or similarity between sequences are generally known in the art, for example, another alignment program is BLAST, used with default parameters. For example, BLASTN and BLASTP can be used using the following default parameters: genetic code=standard; filter= none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR. Details of these programs can be found at the following internet address: http://www.ncbi.nlm.gov/cgi-bin/BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By an HCV "E2 polypeptide" is meant a molecule derived from an HCV E2 region. The mature E2 region of HCV1a begins at approximately amino acid 383–385, numbered relative to the sequence described in Choo et al. (1991) *Proc. Natl. Acad. Sci. USA* 88:2451–2455. A signal peptide begins at approximately amino acid 364 of the polyprotein. Thus, by an "E2 polypeptide" is meant either a precursor E2 protein, including the signal sequence, or a mature E2 polypeptide which lacks this sequence, or even an E2 polypeptide with a heterologous signal sequence. The E2 polypeptide includes a C-terminal membrane anchor sequence which occurs at approximately amino acid positions 715–730 and may extend as far as approximately amino acid residue 746 (see, Lin et al., *J. Virol.* (1994) 68:5063–5073). An E2 polypeptide, as defined herein, may or may not include the C-terminal anchor sequence or portions thereof. It should be noted that the term an "E2 polypeptide" as used herein is not limited to the HCV 1a sequence. In this regard, the corresponding E2 regions in other HCV isolates can be readily determined by aligning sequences from the isolates in a manner that brings the sequences into maximum alignment. This can be performed with any of a number of computer software packages, such as ALIGN 1.0, available from the University of Virginia, Department of Biochemistry (Attn: Dr. William R. Pearson). See, Pearson et al., *Proc. Natl. Acad. Sci. USA* (1988) 85:2444–2448. Thus, the term encompasses E2polypeptides from any of the various HCV strains and isolates including isolates having any of the 6 genotypes of HCV described in Simmonds et al., *J Gen. Virol.* (1993) 74:2391–2399 (e.g., strains 1, 2, 3, 4 etc.), as well as newly identified isolates, and subtypes of these isolates, such as HCV1a, HCV1b etc.

The phrase "stably replicating" as used herein in reference to the sub-genomic replicons means the steady, continuous generation of new sub-genomic replicons in the cells into which initial sub-genomic replicon transcripts are transfected, as well as their progeny cells. The transfected cells continue to proliferate, and the sub-genomic replicons continue to replicate.

The term "cell" as used herein refers to single cells as well as to the collection of cells in cultures derived from a single progenitor cell, otherwise referred to as cell lines.

As used in this specification and the appended claims, the singular forms "a," "an" and "the" include plural references unless the content clearly dictates otherwise. Thus, for example, reference to "a cell" includes a mixture of two or more cells. As used herein, the term "comprising" means "including."

As used herein, the term "host anti-viral response factor" refers to any cellular gene, control element, protein, or the like that becomes activated, expressed, or is otherwise affected in response to the presence of viral infection within the cell, as a part of the cellular response aimed at eliminating the virus. Examples of such host anti-viral response factors include interferons (IFNs) and interferon-induced genes, such as PKR and 2'-5' oligoadenylate synthetase.

As used herein, "host viral response helper factor" refers to cellular genes, proteins and other molecules which may be harnessed by a virus, or by viral proteins, for viral replication activities. Thus, "host viral response helper factors" may be targets of compounds that modulate viral replication. Typically, these are host cell housekeeping genes and gene products that are used by the virus in the replication cycle. Examples of cellular gene products known to be harnessed by HCV in its replication cycle, include the La autoantigen (Ali & Siddiqui, 1997, Proc. Natl. Acad. Sci. USA, 94:2249–54), polypyrimidine tract-binding protein (PTB) (Gontarek et al., 1999, Nucleic Acids Res., 27:1457–63), and the eIF2Bγ and eIF2γ subunits (Kruger et al., 2000, Proc. Natl. Acad. Sci. USA, 97:8566–8571). The La autoantigen and PTB are also known to be harnessed by other positive-strand RNA viruses, including poliovirus, Sindbis virus, and bovine viral diarrhea virus (BVDV).

As used herein, "PKR activity" refers to any of the functions of PKR, including, without limitation, autophosphorylation, phosphorylation of eIF2α, and induction of apoptosis.

As used herein, the term "PKR-deficient" in reference to cells means cells in which PKR activity is disabled.

As used herein, the terms "disable" and "disabling" in reference to host anti-viral response factors or PKR activities refer to any interference with normal response or activity. For example, the terms "disable" and "disabling" include both the elimination and reduction of PKR activity. The disabling of PKR activity can occur prior to or concurrent with transfection of the sub-genomic viral replicons. The disabling of PKR activity can be monitored in many ways, including, but not limited to, measurements of PKR phosphorylation activity (including autophosphorylation), reduction and/or prevention of apoptosis of the cells, and reduction and/or blocking of interferon induction of NF-κB-dependent reporter gene expression.

As used herein, the term "compound" means any identifiable chemical or molecule, including, but not limited to small molecules, peptides, polypeptides, proteins, sugars, nucleotides, or nucleic acids. Such compounds can be natural or synthetic.

As used herein, the term "modulates" in reference to host anti-viral response factors or PKR activity means results in a change in the amount, quality, or effect of a particular response or activity. Both increases and decreases in the response or activity are included.

One aspect of the invention is directed to generating cells, with a disabled host anti-viral response factor activity, that stably replicate sub-genomic virus replicons. For example, cells with a disabled interferon response would also present favorable environments for stable replication of sub-genomic viral replicons, because the interferon response is upstream of PKR. Further details on the interferon response pathway are provided in J. Vilcek & G. C. Sen, Interferons and Other Cytokines, Chapter 13, p. 375–400, In Virology (Fields), 3rd Ed., Lippincott-Raven Pubs. (1996).

Another aspect of the present invention is directed to generating cells with disabled PKR activity, i.e., PKR-deficient cells, that stably replicate sub-genomic virus replicons. Preferably, the invention is directed to generating cells, with disabled PKR activity, that stably replicate sub-genomic HVC replicons.

There are various approaches that can be used to disable PKR activity, and thereby facilitate the establishment of cell clones that present a favorable environment for replication of stably-maintained HCV sub-genomic replicons. Methods of disabling PKR activity include, but are not limited to: 1) generation of stable cell lines containing a dominant-negative PKR; 2) alteration of the genomic copy of the PKR gene (which may be accomplished by changing 1 or 2 nucleotides) using chimeric DNA/RNA oligonucleotides, according to methods of Kren et al., 1997, Hepatology, 25:1463–1468 and Culver et al., 1999, Nature Biotechnology, 17:989–993; 3) inhibition of PKR activity with 5-amino purine (5-AP); 4) overexpression of $p58^{IPK}$, a cellular protein, which is a known inhibitor of PKR (Lee et al., 1990, Proc. Natl. Acad. Sci. USA, 87:6208–6212; Barber et al., 1994, Proc. Natl. Acad. Sci. USA, 91:4278–4282); 5) overexpression of HCV envelope 2 (E2) protein, also shown to inhibit PKR (Taylor et al., 1999, Science, 285:107–110); and 6) inhibition of PKR translation through the use of antisense nucleic acids to PKR message.

In one embodiment of the invention, a cell is stably transfected with a nucleic acid construct encoding a dominant-negative mutant of PKR, prior to introduction of a sub-genomic viral replicon. Dominant-negative mutant proteins in cells result in "loss of function" phenotypes by sequestration of the wild-type protein. Dominant-negative mutants of PKR are well known in the art. See, e.g., Salzberg et al., 2000, Exp. Cell Res., 254:45–54; Terenzi et al., 1999, Nuc. Acids Res., 27:4369–4375; Demarchi et al., 1999, J.

Virol., 73:7080–7086; Shang et al., 1998, J. Biol. Chem., 273:30608–30613; Nagai et al., 1997, J. Virol., 71:1718–25; Ortega et al., 1996, Virology, 215:31–39; Der & Lau, 1995, Proc. Natl. Acad. Sci. USA, 92:8841–8845; Koromilas et al., 1992, Science, 257:1685–1689. In a non-limiting example, the dominant-negative mutant of PKR is the catalytically inactive [$Arg^{296}$]-PKR mutant. Any dominant-negative mutant of PKR which behaves similarly to sequester and block out wild-type PKR protein activity is contemplated as a dominant-negative mutant of PKR for use in the invention.

Cells expressing dominant-negative mutants of PKR can be prepared by any of a variety of techniques, including, but not limited to, use of a stably maintained, drug selectable plasmid expression vector, integration of the nucleotide sequences encoding the dominant-negative PKR into the cellular DNA, and use of an inducible expression system. In one embodiment of the invention, the dominant-negative PKR gene is expressed from a zeocin-selectable expression vector, and cells expressing the dominant-negative PKR are selected in zeocin. Many other selectable markers known to the art can be used for such selection schemes.

In another embodiment of the invention, a cell is stably transfected with a nucleic acid construct encoding the p58$^{IPK}$ protein, prior to introduction of a sub-genomic viral replicon. In a non-limiting example, p58$^{IPK}$ with a histidine tag is expressed in the cells from a zeocin-selectable, mammalian expression vector.

In still another embodiment of the invention, a PKR antisense nucleotide is delivered to the cell. By "antisense" is meant a composition containing a nucleic acid sequence which is complementary to the sense strand of a specific nucleic acid sequence. Once introduced into a cell, the complementary nucleotides combine with endogenous sequences produced by the cell to form duplexes and to block either transcription or translation. See, e.g., Agrawal, S., ed. (1996) *Antisense Therapeutics*, Humana Press Inc., Totawa N.J.; Alama et al., 1997, Pharmacol. Res. 36:171–178; Crooke, S. T., 1997, Adv. Pharmacol. 40:1–49; and Lavrosky et al., 1997, Biochem. Mol. Med. 62(1):11–22. Antisense sequences can be any nucleic acid material, including DNA, RNA, or any nucleic acid mimics or analogs. See, e.g., Rossi et al., 1991 Antisense Res. Dev. 1:285–288; Pardridge et al., 1995, Proc. Nat. Acad. Sci. 92:5592–5596; Nielsen and Haaima, 1997, Chem. Soc. Rev. 96:73–78; and Lee et al., 1998, Biochemistry 37:900–1010. Delivery of antisense sequences can be accomplished in a variety of ways, such as through intracellular delivery using a recombinant vector.

Antisense oligonucleotides of about 15 to 25 nucleic acid bases are typically preferred as such are easily synthesized and are capable of producing the desired inhibitory effect. Molecular analogs of antisense oligonucleotides may also be used for this purpose and can have added advantages such as stability, distribution, or limited toxicity. In addition, chemically reactive groups, such as iron-linked ethylenediaminetetraacetic acid (EDTA-Fe), can be attached to antisense oligonucleotides, causing cleavage of the RNA at the site of hybridization. These and other uses of antisense methods to inhibit the in vitro translation of genes are well known in the art. See, e.g., Marcus-Sakura, 1988, Anal. Biochem. 172:289.

Sub-genomic viral replicons contain less than the full complement of genes of a viral genome and minimally contain those portions of the viral genome necessary for genome replication. In preferred embodiments of the invention, the sub-genomic replicons are HCV sub-genomic replicons. The construction of several sub-genomic HCV DNA cassettes, using the HCV type 1b genomic backbone, has been described in Lohmann, et al., supra. Such cassettes will have a transcriptional promoter, such as, but not limited to, the T7 RNA promoter, to direct the transcription of sub-genomic replicon RNAs. These sub-genomic replicon RNAs can be transfected into, for example, PKR-deficient cells, to generate cells of the invention that stably replicate sub-genomic virus replicons. HCV sub-genomic replicons of other HCV genomic backbone types, including, but not limited to, the type 1a HCV variant can also be used in the invention. The viral genomic sequence of HCV is known, as are methods for obtaining the sequence. See, e.g., International Publication Nos. WO 89/04669; WO 90/11089; and WO 90/14436. The sequence for the type 1a genome was originally reported in Choo et al., 1989, Science, 244:359–362.

HCV sub-genomic replicons must be capable of directing the translation of the HCV proteins necessary for replication. The 5' untranslated region (UTR) of the HCV genome contains the HCV internal ribosomal entry site (IRES) element, which promotes entry of eukaryotic cellular ribosomes into mRNAs without the involvement of a 5'-terminal capping group. Data from Lu & Wimmer (1996, Proc. Natl. Acad. Sci. USA, 93:1412–1417) and Reynolds et al. (1996, EMBO J., 14:6010–6020) suggest that the bona fide HCV IRES includes genetic information mapping to the 5'NTR and sequences of the HCV open reading frame (ORF).

Using an HCV/polio genomic chimera to study poliovirus replication, Lu & Wimmer found that an efficient HCV IRES element contains not only the sequences from the 5'UTR but also sequences of the adjacent HCV ORF, i.e., nucleotides from the HCV core (C) gene. Inclusion of portions of the HCV core gene, ranging from the first 24 through the first 369 nucleotides of the core gene sequence, supported the replication of the chimeric HCV/polio virus. The chimera containing the first 369 nucleotides of the HCV core gene replicated more efficiently than did chimeras containing shorter regions of the gene. The sub-genomic HCV constructs utilized by Lohmann et al. minimally contained the HCV 5'UTR, followed by the first 36 nucleotides of the C gene.

Non-structural genes NS3, NS4A, and NS5B are known to have defined replication functions, and are probably not dispensable for a replication-competent, HCV sub-genomic replicon. Deletion of NS2, NS4B and NS5A, however, may still yield replication.

In certain embodiments, it is preferred to include a selectable drug resistance marker, such as neo, in HCV sub-genomic replicons for stable maintenance. While not being limited to any particular theory, however, it is believed that a highly active polymerase, for example, may yield higher efficiency replication and alleviate the need for the selectable marker.

In the sub-genomic replicons of HCV described below, most of the structural protein genes are replaced by the selectable marker neo. Other selectable markers can be utilized to allow for selection and maintenance of the cells that contain and support the replication of sub-genomic HCV replicons. Other variations and modifications to the content of sub-genomic replicons of the invention are also contemplated. Modifications include, but are not limited to, deletions of nucleotides, addition of extra nucleotides, and fusions to reporter genes that can serve as detectable markers such as, but not limited to, green fluorescent protein (GFP) and luciferase.

The invention is applicable to the replication of RNAs of other positive-strand RNA viruses, including, but not limited to, alphaviruses, such as Sindbis virus, picornaviruses, such as poliovirus, and Pestiviruses (a genus within the Flaviviridae family), such as bovine viral diarrhea virus (BVDV). Additionally, the invention is applicable to the replication of chimeric sub-genomic replicons of positive-strand RNA viruses, such as, chimeric HCV/polio sub-genomic replicons.

Construction of sub-genomic replicons for other positive-strand RNA viruses is facilitated by known sequence information. The poliovirus genome sequence is provided in Kitamura et al., 1981, Nature, 291:547–553. Sub-genomic replicons of BVDV, used to determine the minimal regions of the genome required for replication, are described in Behrens et al., 1998, J. Virol., 72:2364–2372. Further manipulations of the BVDV genome are described in Vassilev et al., 1997, J. Virol., 71:471–478. Sub-genomic replicons of Sindbis virus, used as expression vectors, are described in Dubensky et al., 1996, J. Virol., 70:508–519. See, e.g., Fields, Knipe, & Howley, eds., Fields Virology, 3$^{rd}$ Edition (Vol. I &II) Lippincott Williams & Wilkins Publishers (1996), for further description of these viruses and other positive-strand RNA viruses.

Selectable drug resistance markers are not required for sub-genomic replicons of Sindbis, poliovirus, and BVDV. While not being limited to any particular theory of operability, selective marker genes may not be required due to the duration of replication cycles of these viruses.

Many different cell types can be used to practice the invention. In a preferred embodiment of the invention, the cell used is a human liver cell. More preferably, the cell is a hepatocellular carcinoma-derived cell. In a non-limiting example, the cell is Huh-7 (Nakabayashi et al., 1982, Cancer Res., 42:3858–3863; Seki et al., 1999, Hepatogastroenterology, 46:2812–2817). In another non-limiting example, the cell is HepG2 (U.S. Pat. No. 4,393,133). Other cell lines in which the invention may be practiced include, but are not limited to, myc immortalized human liver cell lines, and primary cultures of fetal hepatocytes (Sanchez et al., 1995, J. Cell Physiol., 165:398–405).

Another aspect of the invention provides methods of screening for compounds that modulate replication of viral RNAs either directly or indirectly. Compounds can be screened for their effect on the replication of sub-genomic viral replicons in the cells of the invention by treating the cells with test compounds. Compounds that target host viral response factors, harnessed by the virus, within the cell can be identified through such screening. Additionally, compounds that target the viral genes and/or proteins involved in the replication of sub-genomic viral replicons can be identified in such screens. In a preferred embodiment of the invention, compounds that modulate the replication of HCV sub-genomic replicons are identified through screening against cells with disabled PKR activity, in which HCV sub-genomic replicons are stably replicated.

The cells of the present invention can be used to identify compounds that inhibit viral RNA replication, and hence, viral replication, or to identify compounds that enhance viral RNA replication, and hence, viral replication. In particular, compounds identified as having inhibitory effects on the replication of HCV sub-genomic replicons will be candidates for use as drugs in the treatment of HCV infection and disease. Compounds exhibiting replication-enhancing activities will be candidates for use in the development of further cellular and animal model systems of HCV replication.

There are a variety of HCV targets for test compounds, including, but not limited to, HCV internal ribosomal entry sites, HCV NS3 serine proteinase, NS3 RNA helicase, NS5B RNA dependent RNA polymerase, and other HCV non-structural proteins. For example, compounds may interfere with the process of viral replicon replication by interfering with the viral proteins that are critical to RNA replication, all of which are translated off of the transcripts being generated in HCV sub-genomic replicon-containing cells of the present invention.

When a selectable drug resistance marker is included in the sub-genomic replicon, compounds can be assessed for their ability to sensitize cells to the selectable drug, i.e., to render the cells sensitive to the drug that was used to select them. Test cultures where cells die off are indicative of compounds that interfere with replicon replication, because loss of the drug-selectable replicon renders the cells sensitive to that particular drug. Where, for example, a neo resistance marker is used in conjunction with the viral sub-genomic replicon, loss of the neo-selectable, sub-genomic replicon will render the cells sensitive to G418.

The invention is further illustrated by way of the following examples which are intended to elucidate the invention. These examples are not intended, nor are they to be construed, as limiting the scope of the invention. It will be clear that the invention may be practiced otherwise than as particularly described herein. Numerous modifications and variations of the present invention are possible in view of the teachings herein and, therefore, are within the scope of the invention.

EXAMPLES

Example 1

Generating the Dominant-Negative PKR Mutant, [Arg$^{296}$]-PKR

The human PKR coding sequence was cloned using the Marathon cDNA Amplification kit (Clontech) from Marathon human pancreas cDNA (Clontech). RT-PCR was carried out using the following PKR-specific oligonucleotide primers: 5'-AGCTTCCAACCAGGATACGG-3' (SEQ ID NO:1) and 5'-GGCTCTAACATGTGTGTCGTTC-3' (SEQ ID NO:2). The PCR product was cloned into the commercial cloning vector pCR2.1 using the TA cloning kit (Invitrogen), to yield pCR2.1-PKR. The sequence of the PKR cDNA was verified by standard sequencing analyses. PKR active site Lys$^{296}$ was mutated to Arg$^{296}$ using the Quick Change Site-Directed Mutagenesis Kit (Stratagene), and the following primers: 5'-CGGAAAGACTTACGTTATTAGACGTG-TTAAATATAATAACGAGAAGGCGG-3' (SEQ ID NO:3) and 5'-CCGCCTTCTCGTTATTATATTTAACACGTCT-AATAACGTAAGTCTTTCCG-3' (SEQ ID NO:4). The bold and underlined nucleotides indicate the mutational change that creates the DN [Arg$^{296}$]-PKR sequence. Following the mutagenesis, the resultant plasmid is pCR2.1-DNPKR.

The dominant-negative PKR gene was cloned into a mammalian expression vector, pcDNA3.1/GS, containing a zeocin selection marker. The cloning was carried out in two steps. First, a linker sequence, containing BamHI and XbaI sites, was cloned into pcDNA3.1/GS via the vector's DraI and AgeI sites. Second, the DN-PKR gene was excised from pCR2.1-DNPKR by BamHI and XbaI digestion, and subsequently cloned into pcDNA3.1/GS via the introduced BamHI and XbaI restriction sites.

Example 2

Establishing Cells Overexpressing [Arg$^{296}$]-PKR

To establish a Huh-7 cell line expressing [Arg$^{296}$]-PKR, 2×10$^6$ Huh-7 cells were transfected with 2 μg of the Arg$^{296}$ mutant PKR clone using FuGene-6 transfection reagent (Roche Molecular Biochemicals). [Arg$^{296}$]-PKR expressing cells were selected with culture media containing 70 μg/ml zeocin. The selected cell lines are confirmed biochemically by western blot using anti-PKR antibodies, and functionally by testing [Arg$^{296}$]-PKR-mediated suppression of interferon-inducible NF-κB-dependent reporter gene expression.

Example 3

Replicating HCV Sub-Genomic Replicons in [Arg$^{296}$]-PKR-Expressing Huh-7 Cells Three HCV sub-genomic replicons, I$_{377}$neo/NS-3'/wt, I$_{389}$neo/NS3-3'/wt, and I$_{377}$neo/NS3-3'/Δ, identical to three of the cassettes of Lohmann et al., supra, were constructed at Chiron. These are sub-genomic replicons of HCV type 1b (GenBank accession number AJ238799). I$_{377}$ and I$_{389}$ are the designations for HCV IRES variants containing nucleotides 1–377 of the HCV genome (with the first 36 nucleotides of the core gene) and nucleotides 1–389 of the HCV genome (with the first 48 nucleotides of the core gene), respectively. All three cassettes contain genomic sequences spanning from the NS3 gene through the 3'UTR, but the Δ indicates a variant NS5B gene coding for a polymerase containing a 10 amino acid deletion. The "wt" designation indicates a wild type NS5B polymerase (i.e., no deletion).

HCV sub-genomic replicon RNA, bearing the neomycin resistance gene (neo), is synthesized using T7 RNA polymerase MEGAscript kit (Ambion). Following purification, the HCV sub-genomic replicon RNA is transfected into [Arg$^{296}$]-PKR expressing Huh-7 cells by electoporation. The transfected cells are selected with culture media containing 800 μg/ml G418 and 70 μg/ml zeocin. Replication of HCV sub-genomic replicons is verified by Taqman RT-PCR (Roche), northern blot analysis, and protein labeling followed by immunoprecipitation using HCV-specific antibodies.

Example 4

Expression of p58$^{IPK}$ protein in Huh-7 Cells

A zeocin-selectable, mammalian expression DNA vector for p58$^{IPK}$ with a histidine tag (Invitrogen) is transfected into Huh-7 cells and 70 μg/ml zeocin is applied to select p58$^{IPK}$-expressing cells. p58$^{IPK}$ expression is confirmed by western blot using anti-His tag antibodies (Qiagen). Inhibition of PKR by p58$^{IPK}$ is confirmed using the interferon-inducible NF-κB-dependent reporter gene, or by examining IFN-induced PKR autophosphorylation. Establishing stable replication of HCV sub-genomic replicons in p58$^{IPK}$-expressing cells is carried out as described above in Example 3.

Example 5

Inhibition of Cellular PKR Activity With 5-Amino Purine (5-AP)

Huh-7 cells are incubated in medium containing 10 mM 2-AP to inactivate PKR. HCV sub-genomic replicon RNA is prepared and transfected as described above in Example 2. HCV sub-genomic replicon-bearing cells are selected with 800 μg/ml G418. Replication of HCV sub-genomic replicons is analyzed by northern blot, Taqman RT-PCR, and radio-immunoprecipitation.

Example 6

Mutation of Endogenous PKR

PKR function is disabled by alteration of the genomic copy of the PKR gene through targeted nucleotide exchange according to the protocols of Kren et al., 1997, Hepatology, 25:1463–1468 and Culver et al., 1999, Nature Biotechnology, 17:989–993.

Example 7

Screening for HCV Replication Modulators Using HCV Sub-Genomic Replicon Bearing Cells HCV sub-genomic replicon-bearing Huh-7 cells, prepared by any of the above procedures, are employed to screen for compounds that modulate the replication of HCV sub-genomic replicons.

To screen for modulators of replication of HCV sub-genomic replicons, HCV sub-genomic replicon-bearing Huh-7 cells are incubated with media containing a test compound for 0 to 5 days. Cells are harvested, and total RNA is extracted and purified using the RNeasy total RNA kit (Qiagen). HCV sub-genomic replicon RNA is quantified by Taqman RT-PCR. The effect of a test compound is estimated by alteration in HCV RNA titers in the treated cells, as compared with untreated controls. HCV RNA titers are decreased when a compound inhibits viral RNA replication; HCV RNA titers are increased when a compound enhances viral RNA replication.

Example 8

Screening for HCV Replication Inhibitors Using HCV Sub-Genomic Replicon Bearing Cells Alternatively, test compounds are assayed for their ability to sensitize cells to neomycin treatment, i.e., cell viability under test inhibitor compound and G418 treatment.

Example 9

Replicating Sindbis Virus Sub-Genomic Replicons in [Arg$^{296}$]-PKR-Expressing Huh-7 Cells Sindbis virus sub-genomic replicon contruct, pRSIN-β-gal was obtained from T. Dubensky at Chiron). The genome organization and construction of pRSIN-β-gal is described in Dubensky et al., 1996, J. Virol., 70:508–519. The viral capsid and envelope genes are replaced by the β-galactosidase gene (β-gal) in this sub-genomic replicon. RNA transcripts of the sub-genomic replicon are generated by in vitro transcription from the SP6 promoter in the construct. Sub-genomic replicon RNAs are transfected into [Arg$^{296}$]-PKR-expressing Huh-7 cells. Replication is monitored as described in Dubensky et al.

Example 10

Replicating Poliovirus Sub-Genomic Replicons in [Arg$^{296}$]-PKR-Expressing Huh-7 Cells Two different Poliovirus (PV) sub-genomic DNA replicon cassettes are constructed. In each, the capsid protein gene is replaced with a reporter gene, either the luciferase (Luc) marker gene, or a green fluorescent protein (GFP) gene. The organization of the sub-genomic replicons is as follows: PV 5'UTR-Luc (or GFP)-PV non-structural proteins (2A, 2B, 2C, 3A, 3B, 3C, 3D)-PV 3'UTR. Sub-genomic PV replicon RNA transcripts of the two different constructs are generated in vitro, and separately transfected into [Arg$^{296}$]-PKR-expressing Huh-7 cells. Replication levels are monitored as described in Lu & Wimmer, supra.

Example 11

Replicating BVDV Sub-Genomic Replicons in [Arg$^{296}$]-PKR-Expressing Huh-7 Cells A bovine viral diarrhea virus (BVDV) sub-genomic replicon cassette is constructed, with an in-frame partial deletion of the E1 and E2 envelope genes. The E0 envelope gene, core (C) gene, and all of the nonstructural genes are maintained. The organization of the replicon is as follows: BVDV 5'UTR-N$^{pro}$-C-E0-E1 (C-terminal 162 amino acids deleted)-E2 (N-terminal 123 amino acids deleted)-p7-NS2 through NS5B-3'UTR. The in-frame deletion in the E1-E2 region should yield a BVDV replicon. Sub-genomic BVDV replicon RNA transcripts are generated in vitro as described by Behrens et al., supra. Sub-genomic replicon RNAs are transfected into [Arg$^{296}$]-PKR-expressing Huh-7 cells and replication levels are monitored as described in Behrens et al., supra.

We claim:

1. A method of screening for compounds that modulate viral replication comprising the steps of
   a) administering a test compound to a cell, wherein said cell comprises a replicating sub-genomic viral replicon, and further wherein said cell is PKR deficient, and
   b) determining whether said test compound modulates the replication of said sub-genomic viral replicon.

2. A method of screening for compounds that inhibit viral replication comprising the steps of
   a) administering a test compound to a cell, wherein said cell comprises a replicating sub-genomic viral replicon, and further wherein said cell is PKR deficient, and
   b) determining whether said test compound inhibits the replication of said sub-genomic viral replicon.

3. The method of claim 1, wherein the sub-genomic viral replicon is a HCV sub-genomic replicon.

4. The method of claim 3, wherein the HCV sub-genomic replicon comprises all of the non-structural HCV genes and none of the structural HCV genes.

5. The method of claim 2, wherein the sub-genomic viral replicon is a HCV sub-genomic replicon.

6. The method of claim 5, wherein the HCV sub-genomic replicon comprises all of the non-structural HCV genes and none of the structural HCV genes.

* * * * *